United States Patent [19] [11] Patent Number: 4,846,813
Raley [45] Date of Patent: Jul. 11, 1989

[54] SELF-SEALING FLUID ABSORBENT ARTICLE
[75] Inventor: John M. Raley, Appleton, Wis.
[73] Assignee: Kimberly-Clark Corporation, Neenah, Wis.
[21] Appl. No.: 779,904
[22] Filed: Sep. 25, 1985
[51] Int. Cl.[4] .............................................. A61F 13/16
[52] U.S. Cl. .................................. 604/385.1; 604/378
[58] Field of Search ............... 604/358, 365, 366, 368, 604/370, 378, 385.1, 383, 367, 371, 372, 374, 375

[56] References Cited
U.S. PATENT DOCUMENTS

| | | | |
|---|---|---|---|
| 3,814,101 | 6/1974 | Kozak | 604/370 |
| 3,886,941 | 6/1975 | Duane | 604/370 |
| 3,888,256 | 6/1975 | Studinger | 604/368 |
| 3,929,135 | 12/1975 | Thompson | 604/385.1 |
| 4,429,001 | 1/1984 | Kolpin et al. | 428/283 |

Primary Examiner—John D. Yasko
Assistant Examiner—Denise Whelton
Attorney, Agent, or Firm—Paul Yee

[57] ABSTRACT

A fluid absorbent article, comprising an absorbent web expandable upon fluid absorption and joined to a topsheet of fluid impervious material having a plurality of tapered passages therein, each open at its respective base and apex, and oriented with its base in the plane of the topsheet and its apex disposed in an interior portion of said absorbent web, such that fluid contacting the topsheet, surface tensionally enters the tapered passages at the bases thereof for passage therethrough to exit at the apexes thereof into the absorbent web, whereupon expansion of the absorbent web in proximity to the tapered passages compressively affects closure thereof to sealingly retain the fluid in the absorbent web. Such article is applicable to a method of absorbing fluids in a corporeal environment, comprising the step of contacting the topsheet with the fluid, surface tensionally flowing the fluid into the absorbent web through the tapered passages, and expanding the web to compressively close the tapered passages and sealingly retain fluid in the absorbent web.

30 Claims, 1 Drawing Sheet

SELF-SEALING FLUID ABSORBENT ARTICLE

BACKGROUND OF THE INVENTION

1. Field Of The Invention

This invention relates generally to a fluid absorbent article and to a method for absorbing fluids, such as pus, urine or menstrual fluids, in a corporeal environment.

2. Description Of The Related Art

In the field of absorbent articles, there has been an ongoing effort to provide improved articles of the type comprising an absorbent web joined to a topsheet, for use in applications such as disposable diapers, sanitary napkins, incontinence pads, and the like, whereby fluids may quickly and efficiently be sorbed. A specific problem associated with numerous absorbent articles developed to date for such applications involves flow-back of previously sorbed fluid from the absorbent web. Considering a disposable diaper as an illustration, when a baby sits or moves while wearing the diaper, significant pressure is exerted on portions of the absorbent web and causes the exudation of previously sorbed fluid therefrom, whereby the fluid may be brought in contact with the baby's skin, resulting in excessive skin wetness, diaper rash, infection of scratches or lacerations in the diaper wearing area, etc. Accordingly, a variety of designs and configurations of absorbent articles has been proposed and/or employed in the prior art to overcome such problem, so that the topsheet associated with the absorbent web is kept dry in use, consistent with retention of the sorbed fluid in the absorbent web, despite pressure or deforming forces exerted thereon.

U.S. Pat. Nos. 3,814,101 and 3,886,941 issued to T. F. Kozak and J. J. Duane, et al., respectively, disclose a disposable absorbent article useful in diapers, incontinence pads and the like, which is said to readily permit flow of liquid in the direction of the absorbent layer through the topsheet associated therewith, but which substantially reduces the possibility of flow in the opposite direction. The topsheet may be formed from a non-fibrous hydrophobic material such as thermoplastic film, and features a plurality of valvular apertures therein. These valvular openings may be of two basic types, substantially straight slits and punctures. An array of dimple depressions is situated across the surface of the topsheet. The patent states that the configuration of these dimples can be circular, elliptical, rectangular, diamond-shaped, and the like, the important criteria being that they are formed so that there is substantially no breaking or cutting of the topsheet during or after fabrication. The slits are disclosed as being from about 0.030 to about 0.25 inch in length, at a density of from about 30 to about 150 slits per square inch.

The dimples in the above-described system extend below the plane of the topsheet a short distance, so that the absorbent material immediately below the dimples is in a compressed state. The arrays of respective slits and dimples intersect so that where a dimple is formed over a portion of a slit, the slit is stated to be open to a much greater degree than the corresponding slits situated remote from the dimples on the topsheet's surface. Likewise, the slits disposed between corresponding dimples are said to be open to a greater extent than would be the case if no dimples were present. In use, as liquid is transferred to the absorbent pad through the slits, the absorbent pad absorbs the liquid through its entire area until either partial or full saturation is achieved. The compressed material expands during the sorption and urges the dimples upward, closer to the plane of the topsheet. This action serves to close the previously opened slits, thereby trapping the liquid in the absorbent pad. As a general rule, it is stated that the total area occupied by the dimples should not occupy more than about 20% of the area of the absorbent material. The patent indicates that the absorption of liquid is accomplished through the valvular slits as contrasted to absorption through the thermoplastic topsheet in the non-ruptured depressed areas.

U.S. Pat. No. 3,888,256 to H. Studinger describes a multilayer absorbent pad, wherein an upper layer is a plastics-bound fibre fleece or web, beneath which there is disposed at least one layer of cellucotton acting as a filter layer and preventing the underlying material from escaping from the absorbent pad. Beneath the layer(s) of cellucotton there is disposed at least one layer of a swelling substance which may be powdery or granular in form and consists of polyacrylamide, sulphonated polystyrene or other suitable substance, which may be fixed, e.g., adhered, to a carrier sheet of cellucotton. Beneath the layer of sewlling substance there is disposed a relatively thick layer which may be one or more layers of cellulose wadding. Crepe paper or cellucotton may be utilized in this layer in place of cellulose wadding. Finally, there is disposed a bottom layer which may also consist of at least one surface layer of cellucotton, plastics-bound fibre fleece or liquid-impervious foil, such as polyethylene foil. In operation, liquid impinging on the upper surface layer of the pad will penetrate thereinto and leak into the absorbent layer of cellulose wadding, crepe paper or cellucotton. Resulting contact of the liquid with the swelling substance layer causes the particles therein to swell and coalesce into a jelly-like liquid impervious layer, creating a barrier for the liquid already present in the absorbent layer. Subsequent squeezing or pressure imposed on the absorbent pad will not result in expression of liquid out of the absorbent layer, so that the article remains dry even if subjected to violent treatment resulting in considerable surface deformation of the pad.

U.S. Pat. No. 4,429,001 to E. E. Koltin, et al discloses absorbent sheets prepared from a coherent web of entangled blown fibers formed by extruding liquid fiber-forming material into a high-velocity gas stream. An array of superabsorbent polymeric particles is dispersed within the web. Sheet products of such materials will expand greatly in size during sorption, the constituent fibers typically increasing in thickness by a factor of 10. The fibers employed in this nonwoven matrix may be derived from polypropylene, polyethylene, polyethylene terephthalate, and polyamides. These materials are disclosed to be suitable for forming meltblown fibers. Alternatively, the fibers may be formed by solution blowing, from materials such as polymers or copolymers of vinyl acetate, vinyl chloride, and vinylidene fluoride. Inorganic materials also are disclosed as suitable for forming the fibers. The absorbent materials in the matrix may comprise modified starches, and high molecular weight acrylic polymers containing hydrophilic groups. For liquids other than water, alkylstyrene absorbent particles may be employed.

U.S. Pat. No. 3,929,135 H. A. Thompson, discloses an absorptive article suitable for applications such as diapers, sanitary napkins, incontinence pads, and the like, comprising a fluid-impervious topsheet material provided with tapered capillaries, each of which has a base in the plane of the topsheet and an apex remote from the plane, the apex being in intimate contact with an absorbent element. The angle of taper of the capillaries is from about 10° to about 60°, the base opening dimension is from about 0.006 to about 0.250 inch, and the apex opening dimension is from about 0.004 to about 0.100 inch. Such topsheet is alleged to allow the free transfer of fluids from the body contiguous thereto, into the absorbent element of the device while inhibiting the reverse flow of these fluids. The topsheet is constructed of a liquid impervious material such as low density polyethylene at a thickness of 0.001–0.002 inch. The capillaries may be in the form of a frustum of a conical surface, pyramid or similar body with a triangular, square or polygonal base; additionally, they may be asymmetric, and the angle of taper may change continuously from the base to the apex thereof. Capillaries also may be provided in the form of slots having sides and ends tapered at angles analogous to circular capillaries. Capillary base diameters must be small enough to allow a liquid droplet to bridge across at least one capillary. The patent states at column 4, lines 50-52 that the height of the tapered capillary should provide a structure wtih a minimum tendency to collapse in use. The criterion that no reverse flow of fluid occurs in the absorbent element when same is placed under pressure, is achieved by having the absorbent element constructed so that less than the full saturation level is reached in use. In other words, the absorbent element is designed and constructed to contain a significantly larger quantity of fluid than is anticipated that the device will be required to contain in a practical use situation. The absorbent pad may comprise any suitable absorbent material such as comminuted wood pulp (airfelt), crepe cellulose wadding, etc.

The prior art thus has proposed a variety of absorptive structures and absorbent articles for applications such as sanitary napkins, disposable diapers and the like. However, all of the aforementioned prior art teachings are characterizable by deficiencies in fabrication and/or in use, insofar as the objective is concerned with providing a sorbent article which sorbs fluid to keep a topsheet or upper layer of the article dry. For example, the absorbent articles disclosed in the aforementioned U.S. Pat. Nos. 3,814,101 and 3,886,941, comprising a plurality of valvular aperatures and a system of dimples disposed across the surface of a topsheet, represent a comparatively complex structure insofar as the topsheet fabrication and processing steps are concerned. The five-layered composite of U.S. Pat. No. 3,888,256 is complex in terms of its many constituent elements, and thus is likely to have a high production cost. The sorbent sheet product of U.S. Pat. No. 4,429,001 does not disclose an application to any structure which will provide a dry topsheet surface. The absorptive article of U.S. Pat. No. 3,929,135 represents a generally efficient structure insofar as the topsheet is concerned, however in meeting the objective of effectively inhibiting the reverse flow of fluids from the absorbent element, the article must, as disclosed, provide an excess of the absorbent so that its sorptive capacity is not exceeded. Accordingly, the provision of absorbent in such system must be subject to a large safety factor, insofar as the amount of sorbent material is concerned, to assure that even under high fluid loading conditions in use, the absorbent is not so saturated as to exclude fluid when placed under pressure, such as where an infant is sitting or moving about in a wet disposable diaper.

Accordingly, it is an object of the present invention to provide an improved fluid absorbent article, of the type wherein a topsheet is joined to an absorbent material.

It is another object of the present invention to provide a fluid absorbent article of such type, which is comparatively simple in construction and of low fabricational cost.

It is a further object of the present invention to provide a fluid absorbent article wherein a minimum quantity of absorbent material is necessary.

Other objects and advantages of the present invention will be apparent from the ensuing disclosure and appended claims.

SUMMARY OF THE INVENTION

In one aspect, the present invention relates to a fluid absorbent article, comprising an absorbent web expandable upon fluid absorption and joined to a topsheet of fluid impervious material having a plurality of tapered passages therein, each open at its respective base and apex, and oriented with its base in the plane of the topsheet and its apex disposed in an interior portion of the absorbent web, such that fluid contacting an outer surface of the topsheet, surface tensionally enters the tapered passages at the bases thereof for passage therethrough to exit at the apices thereof into the absorbent web, whereupon expansion of the absorbent web in proximity to the tapered passages compressively effects closure thereof to sealingly retain the fluid in the absorbent web.

In another aspect, the present invention relates to a method for absorbing fluid in a corporeal environment, comprising the steps of:

providing an absorbent web expandable upon fluid absorption and joined to a topsheet of fluid impervious material having a plurality of tapered passages therein, each open at its respective base and apex, and oriented with its base in the plane of the topsheet and its apex disposed in an interior portion of the absorbent web;

contacting the topsheet with the fluid;

surface tensionally flowing the fluid into the absorbent web through the tapered passages in the topsheet; and expanding the web by absorption of the fluid to compressively close the tapered passages and sealingly retain the fluid in the absorbent web.

BRIEF DESCRIPTION OF THE DRAWINGS

The features and elements of the present invention will be more fully apparent from the appended drawings, wherein:

FIG. 1 is a partial sectional perspective view of a fluid absorbent article according to the present invention, such as may be usefully employed as a sanitary napkin, disposable diaper, incontinent pad, or the like.

DETAILED DESCRIPTION OF THE PREFERRED EMBODIMENTS

Figure 1:
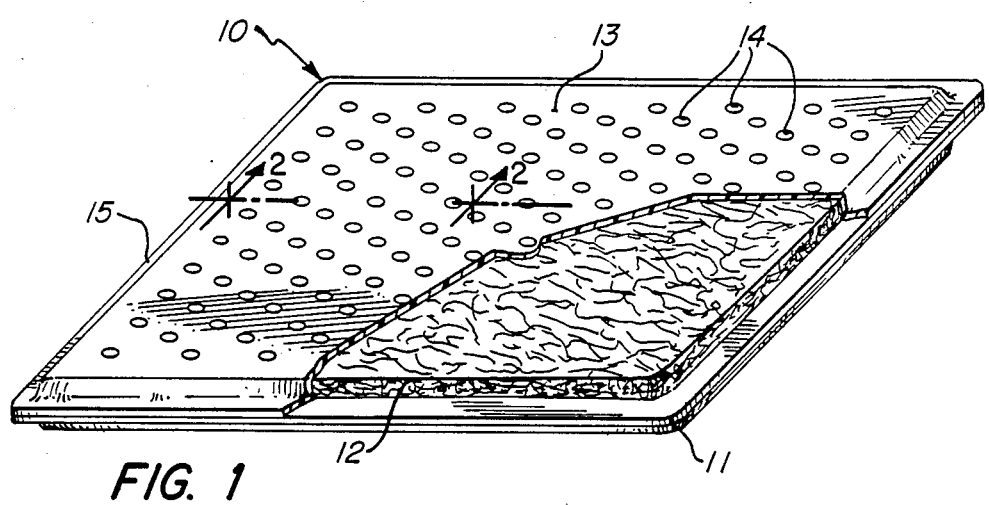

Referring now to FIG. 1, there is shown a fluid absorbent article 10 which as indicated is of a type suitable for use in applications such as disposable diapers, sanitary napkins, incontinence pads, and the like. The absorbent article comprises a fibrous, absorbent web 12 of sheet-like form, expandable upon fluid absorption, as described more fully hereinafter.

The absorbent web 12 is joined, e.g., positioned contiguously, or bonded adhesively or otherwise, to the topsheet 13 of fluid impervious material having a plurality of tapered passages 14 therein. The topsheet 13 is generally coextensive with a bottom sheet or backsheet 11, and may be bonded thereto at the marginal portions 15 of these respective sheets, as is common practice in the art.

As mentioned the topsheet may be disposed in contiguous contact with the absorbent web, or may be bonded, adhered or affixed thereto, all such variants being intended as included within the scope of the term "joined". It will be appreciated, however, that in instances where the absorbent web is bonded at its top surface to the topsheet 13, the adhesive or bonding medium should not be so extensively applied as to occlude any significant area of the fibrous web surface. Accordingly, it is preferred to join the topsheet to the absorbent web by simple juxtaposition in the manner shown, where the topsheet is retained in position by being bonded marginally to a bottom sheet. Alternatively, the topsheet marginal areas could be folded underneath the web and adhesively bonded or otherwise affixed to the web on the bottom surface thereof. In some instances it may be advantageous to provide a topsheet of greater length and width than the absorbent web and simply to enfold the web with the topsheet, whereby the respective ends of the topsheet are joined to one another on the underside of the absorbent web, thereby obviating the need for a separate bottom sheet. In other instances, it may be suitable to provide merely a topsheet of the form shown in FIG. 1, and to dispense with the provision of a bottom sheet or backsheet. In most cases, however, it is advantageous to employ both a topsheet and a bottom sheet.

Figure 2:
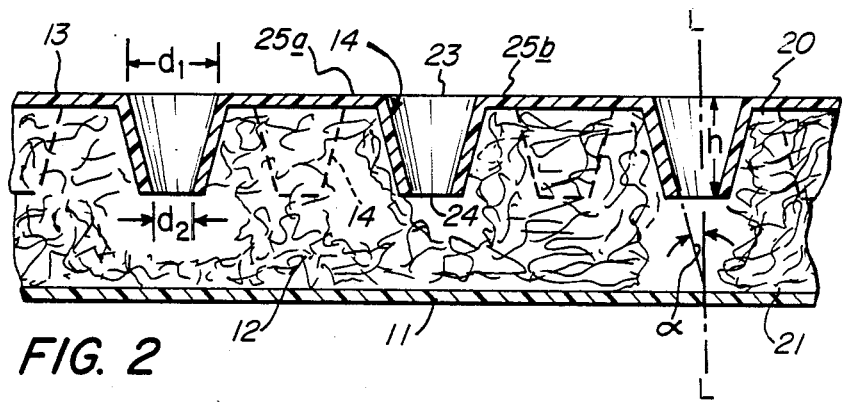
FIG. 2 is a sectional elevational view of a portion of the article taken along line 2—2 of FIG. 1.

Referring to FIG. 2, there is shown a sectional elevational view of a portion, taken along the line 2—2, of the FIG. 1 absorbent article. The elements shown in FIG. 2 are numbered correspondingly with respect to the same system elements in FIG. 1. The topsheet 13 may be of a suitable fluid impervious material, such as for example polypropylene, polyethylene, polyvinylchloride, and polyvinylidene chloride, or any other satisfactory material, having the desired surface characteristics and material characteristics for the intended use. The topsheet has a plurality of tapered passages 14 therein, each open at its respective base and apex, and oriented with its base in the plane of the topsheet and its apex disposed in an interior portion of the fibrous web 12. Thus, in the embodiment shown, the tapered passages have circular openings at their respective base and apex extremities, with the opening of the base end thereof defining a base opening dimension $d_1$, which may for example be on the order of about 0.006–0.400 inch. The apex opening may define an opening dimension $d_2$, of about 0.004–0.300 inch. The height of the tapered passage, as measured along the centerline L—L thereof and denoted in FIG. 2 as dimension h, may be about 0.003–0.20 inch. The tapered passages 14 are shown in FIG. 2 as being constituted by inverted frusto-conical passages, however the utility of the invention is not limited to such geometry, and the cross-section of the passage at the base and apex extremities may be any suitable non-circular shape, such as square, triangular or polygonal, either symmetric as shown with respect to the bounding sidewalls or asymmetric, with arcuate or other non-linear shaped sidewalls. The opening dimensions of the base and apex openings associated with the tapered passages are the respective longest distances between opposite sidewall segments bounding the openings, as measured at the base opening in the plane of the topsheet and at the apex opening in the plane generally containing the apex opening. The inverted frusto-conical tapered passages in FIG. 2 are symmetrical in form and define an included angle, alpha, between the sidewall surfaces and the longitudinal axes L—L of the tapered passages. In instances where the sidewalls of the tapered passages are non-linear, e.g., arcuate, the included wall angle is suitably measured at the apex opening, by a tangent to the wall at such point. In the case of a symmetrical inverted frusto-conical passage as shown in FIG. 2, the angle alpha may suitably range from about 10° to about 70°. Thus, the tapered passages are disposed in a regular array across the surface of the topsheet as shown in FIG. 1, with each passage 14 being surrounded by topsheet surface portions 25a and 25b which lie in the plane of the topsheet, and are devoid of any fluid openings, such as slits, slots or other apertures. Alternatively, the tapered passages may be disposed in an irregular or random array across the surface of the topsheet. The fibrous web is joined at its top surface 20 to the topsheet 13, which as indicated may be a simple positional juncture wherein the topsheet and fibrous web are contiguous to one another but are not in any way adhered or otherwise bonded to one another. At its lower surface 21, the fibrous web 12 is joined to the bottom sheet, in the manner previously mentioned, i.e., either being disposed in contiguous relationship thereto or being otherwise bonded or permanently affixed to the bottom sheet.

Although the tapered passages are shown in FIG. 1 as being distributed in a regular pattern on the surface of the topsheet, it will be appreciated that other patterns and arrays of such passages may be utilized to good effect. The specific density or concentration of tapered passages per unit area of topsheet may vary across the surface thereof, in accordance with the specific end use of the absorbent article. For example, in application to disposable diaper end uses, the article as shown in FIG. 1 could be modified whereby the fluid openings 23 (base openings) in the topsheet may be concentrated at a higher density in the central region of the article, in a central longitudinally extending strip of the topsheet, with the transverse marginal areas of the topsheet laterally adjacent such longitudinal central strip being provided with tapered passages at a reduced concentration or even at a zero concentration, such that the sheet in such marginal areas is imperforate. The specific arrangement and open area provided by the tapered passages in any given region of the topsheet will be a function of the specific end use application, as well as the dimensions of the tapered passages and the characteristics of the absorbent web. Accordingly, in any given application, one of ordinary skill may readily determine the specific arrangement and density of the tapered passages necessary or desirable for the various regions of the topsheet, or for the topsheet as a whole, by the simple expedient of a few tests carried out at varying open area and tapered passage dimensions.

It is a critical feature of the present invention that the absorbent web is expandable upon fluid absorption.

Figure 3:
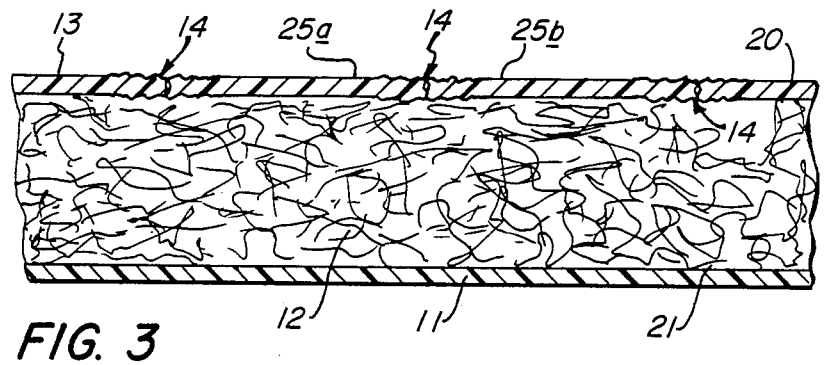
FIG. 3 is a sectional elevation view of a portion of the absorbent article corresponding to the view of FIG. 2, but wherein the tapered passages of FIG. 2 have been compressively closed by expansion of the absorbent web upon absorption of fluid by the web.

FIG. 3 shows a sectional elevational view of a portion of the absorbent article corresponding to FIG. 2, but viewed subsequent to the absorption of fluid by the absorbent web of the FIG. 2 article. Again considering the FIG. 2 article, fluids such as pus, urine or menstrual fluid, or other fluid contacting the topsheet upper surface, surface tensionally flows through the tapered passages 14 for sorption by the absorbent web 12, whereby the absorbent web expands to compressively close the tapered passages 14. The absorbent web thus upon expansion attendant the sorption of fluid compressively collapses the tapered passages, with the sidewalls thereof being forced generally into the plane of the topsheet, as shown in FIG. 3, to seal the topsheet and thereby sealingly retain the fluid in the absorbent web.

The absorbent web expandable upon fluid absorption may be formed of any suitable absorbent materials of such character, as known in the art, for example those materials disclosed in the aforementioned U.S. Pat. Nos. 3,888,256; 3,886,941; 3,814,101; 4,429,001, the disclosures of which are incorporated herein to the extent pertinent. Thus, the absorbent web may be formed of materials such as hydrogels, cellulosic fluff, rayon, polyester, nylon, polypropylene, and mixtures of two or more such materials. Suitable hydrogel materials may include carboxymethylcellulose, polyacrylamides, sulfonated polystyrenes, polyethylene oxide, polyethylene imine, and polymeric materials containing repeating units selected from the group consisting of

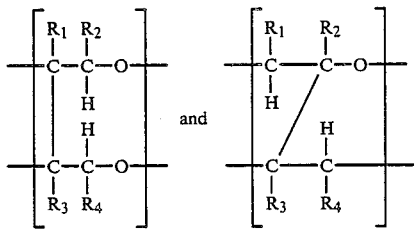

wherein $R_1$–$R_4$ are selected from the group consisting of hydrogen, methyl, phenyl and vinyl radicals. A particularly preferred absorbent web utilizable in the broad practice of the present invention is a nonwoven matrix of cellulosic fibers wherein polyacrylate powder is generally uniformly dispersed through the matrix, or a superabsorbent material of the type as disclosed in the aforementioned U.S. Pat. No. 4,429,001.

It will be appreciated from the foregoing, that the topsheet of the present invention may be readily formed by the process of pin molding, as disclosed in U.S. Pat. No. 3,929,135. The absorbent article of the present invention is highly efficient in use, and overcomes the problem of reverse flow of the fluid sorbed by the absorbent, in the provision of a web of absorbent material expanding upon fluid absorption and a topsheet with pressure-reclosable openings therein, whereby fluid may be sealingly retained in the absorbent web, with a comparatively minimum quantity of absorbent, as compared to prior art systems, e.g., the absorbent article described in U.S. Pat. No. 3,929,135 wherein an excess quantity of absorbent material must be provided in order to prevent a reverse flow of the fluid sorbed into the absorbent web.

Although preferred embodiments of the invention have been described in detail, it will be appreciated that other modifications, variants and embodiments are possible, and all apparent modifications, variants, and embodiments are to be regarded as being within the spirit and scope of the present invention.

What is claimed is:

1. A fluid absorbent article, comprising an absorbent web expandable upon fluid absorption and joined to a topsheet of fluid impervious material having a plurality of tapered passages therein, each open at its respective base and apex, and oriented with its base in a plane of the topsheet and its apex disposed in an interior portion of the absorbent web, such that fluid contacting an outer surface of said topsheet, surface tensionally enters said tapered passages at the bases thereof for passage therethrough to exit at the apices thereof into said absorbent web, whereupon expansion of the absorbent web in proximity to said tapered passages compressively collapses said tapered passages with sidewalls thereof being forced generally into said plane of the topsheet to close said passages and thereby sealingly retain said fluid in said absorbent web.

2. A fluid absorbent article according to claim 1, wherein said absorbent web is disposed between said topsheet and a fluid impervious backsheet.

3. A fluid absorbent article according to claim 1, wherein said topsheet is formed of a material selected from the group consisting of polypropylene, polyethylene, polyvinylchloride, and polyvinylidene chloride.

4. A fluid absorbent article according to claim 1, wherein said absorbent web is formed of a material selected from the group consisting of hydrogels, cellulosic fluff, rayon, polyester, nylon, polypropylene and mixtures thereof.

5. A fluid absorbent article according to claim 1, wherein said tapered passages are distributed in a regular array across the topsheet surface.

6. A fluid absorbent article according to claim 1, wherein each of said tapered passages has a base opening dimension of about 0.006–0.4 inch, an apex opening dimension of about 0.004–0.3 inch, and a height, measured axially between said base and apex openings, of about 0.003–0.2 inch.

7. A fluid absorbent article according to claim 1, wherein said tapered passages are bounded by sidewalls defining an included angle of between about 10° and 70°, measured between the sidewall surfaces and the longitudinal axes of the tapered passages.

8. A fluid absorbent article according to claim 1, wherein the absorbent web is formed of a hydrogel material selected from the group consisting of carboxymethylcellulose, polyacrylamides, sulfonated polystyrene, polyethylene oxide, polyethylene imine, and polymeric compounds containing repeating units selected from the group consisting of

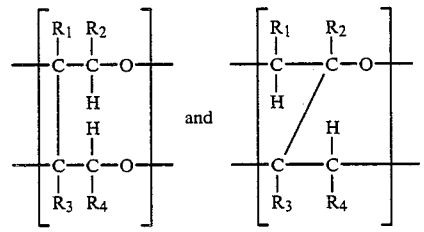

wherein $R_1$–$R_4$ are selected from the group consisting of hydrogen, methyl, phenyl and vinyl radicals.

9. A fluid absorbent article according to claim 1, wherein said absorbent web is a nonwoven matrix of cellulosic fibers containing polyacrylate powder dispersed in said matrix.

10. A method of absorbing fluid in a corporeal environment, comprising the steps of:
providing an absorbent web expandable upon fluid absorption and joined to a topsheet of fluid impervious material having a plurality of tapered passages therein, each open at its respective base and apex, and oriented with its base in a plane of the topsheet and its apex disposed in an interior portion of the absorbent web;
contacting the topsheet with the fluid;
surface tensionally flowing the fluid into the absorbent web through the tapered passages in the topsheet; and
expanding the absorbent web by absorption of the fluid to compressively collapse said tapered passages, with sidewalls thereof being forced generally into said plane of the topsheet to close the tapered passages and sealingly retain the fluid in the absorbent web.

11. A method according to claim 10, wherein the absorbent web is disposed between the topsheet and a fluid impervious backsheet.

12. A method according to claim 10, wherein the topsheet is formed of a material selected from the group consisting of polypropylene, polyethylene, polyvinylchloride and polyvinylidene chloride.

13. A method according to claim 10, wherein the absorbent web is formed of a material selected from the group consisting of hydrogels, cellulosic fluff, rayon, polyester, nylon, polypropylene, and mixtures thereof.

14. A method according to claim 10, wherein each of said tapered passages has a base opening dimension of about 0.006–0.4 inch, an apex opening dimension of about 0.004–0.3 inch, and a height, measured axially between said base opening and said apex opening, of about 0.003–0.2 inch.

15. A method according to claim 10, wherein said tapered passages are bounded by sidewalls defining an included angle in the range of from about 10°–70°, measured between the sidewall surfaces and the longitudinal axes of said tapered passages.

16. A method according to claim 10, wherein said tapered passages are arranged on the surface of said topsheet in a substantially regular array.

17. A method according to claim 10, wherein the absorbent web is a matrix of cellulosic fibers containing polyacrylate powder dispersed therein.

18. A fluid absorbent article according to claim 1, wherein said tapered passages are of inverted frusto-conical shape.

19. A method according to claim 10, wherein said tapered passages are of inverted frusto-conical shape.

20. A fluid absorbent article, comprising:
an absorbent web which is expandable upon fluid absorption; and
a topsheet of fluid impervious material joined onto said absorbent web, said topsheet having surface portions which are devoid of fluid openings and which surround each of a plurality of topsheet portions having tapered passages formed therein, each of said tapered passages open at its respective base and apex, and oriented with its base in a plane of the topsheet and its apex disposed in an interior portion of the absorbent web, such that fluid contacting an outer surface of said topsheet, surface tensionally enters said tapered passages at the bases thereof for passage therethrough to exit at the apices thereof into said absorbent web, whereupon expansion of the absorbent web in proximity to said tapered passages compressively collapses said tapered passages, with sidewalls thereof being forced generally into said plane of the topsheet to close said passages and thereby sealingly retain fluid in said absorbent web.

21. A fluid absorbent article according to claim 20, wherein said absorbent web is disposed between said topsheet and a fluid impervious backsheet.

22. A fluid absorbent article according to claim 20, wherein said topsheet is formed of a material selected from the group consisting of polypropylene, polyethylene, polyvinylchloride, and polyvinylidene chloride.

23. A fluid absorbent article according to claim 20, wherein said absorbent web is formed of a material selected from the group consisting of hydrogels, cellulosic fluff, rayon, polyester, nylon, polypropylene and mixtures thereof.

24. A fluid absorbent article according to claim 20, wherein said tapered passages are distributed in a regular array across the topsheet surface.

25. A fluid absorbent article according to claim 20, wherein each of said tapered passages has a base opening dimension of about 0.006–0.4 inch, an apex opening dimension of about 0.004–0.3 inch, and a height, measured axially between said base and apex openings, of about 0.003–0.2 inch.

26. A fluid absorbent article according to claim 20, wherein said tapered passages are bounded by sidewalls defining an included angle of between about 10° and 70°, measured between the sidewall surface and the longitudinal axes of the tapered passages.

27. A fluid absorbent article according to claim 20, wherein the absorbent web is formed of a hydrogel material selected from the group consisting of carboxymethylcellulose, polyacrylamides, sulfonated polystyrene, polyethylene oxide, polyethylene imine, and polymeric compounds containing repeating units selected from the group consisting of

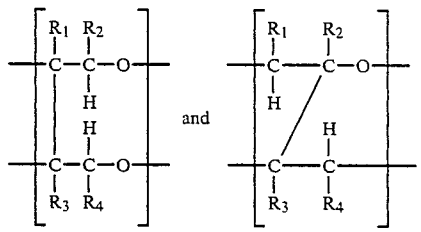

wherein $R_1$–$R_4$ are selected from the group consisting of hydrogen, methyl, phenyl and vinyl radicals.

28. A fluid absorbent article according to claim 20, wherein said absorbent web is a nonwoven matrix of cellulosic fibers containing polyacrylate powder dispersed in said matrix.

29. A fluid absorbent article according to claim 20, wherein said tapered passages are of inverted frusto-conical shape.

30. A method of absorbing fluid in a corporeal environment, comprising the steps of:
providing an absorbent web which is expandable upon fluid absorption;
joining a topsheet of fluid impervious material onto said absorbent web, said topsheet having surface portions which are devoid of fluid openings and which surround each of a plurality of topsheet portions having tapered passages formed therein, each of said tapered passages open at its respective base and apex, and oriented with its base in the plane of a topsheet and its apex disposed in an interior portion of the absorbent web;

contacting the topsheet with the fluid;

surface tensionally flowing the fluid into the absorbent web through the tapered passages in the topsheet; and expanding the absorbent web by absorption of the fluid to compressively collapse said passages, with sidewalls thereof being forced generally into said plane of the topsheet to close said passages and thereby sealingly retain fluid in said absorbent web.

* * * * *